United States Patent [19]

Weeks

[11] Patent Number: 4,520,814
[45] Date of Patent: Jun. 4, 1985

[54] LASER-RESISTANT BACK-UP PAD
[75] Inventor: Vaughan B. Weeks, Racine, Wis.
[73] Assignee: Medical Engineering Corporation, Racine, Wis.
[21] Appl. No.: 426,109
[22] Filed: Sep. 28, 1982
[51] Int. Cl.$^3$ ............................................. A61B 17/36
[52] U.S. Cl. ............................. 128/303.1; 128/132 R; 604/385 R
[58] Field of Search ............ 378/70; 250/516.1, 515.1; 128/132 R, 132 D, 155, DIG. 2, 303.1, 207.14; 604/385, 362; 356/288, 641, 642

[56] References Cited
U.S. PATENT DOCUMENTS 3,185,751 5/1965 Sutton ............................... 250/516.1
3,566,871 3/1971 Richter ................................ 604/362
3,880,500 4/1975 Kojabashian ........................ 350/288
4,378,796 4/1983 Milhaud .......................... 128/207.15

FOREIGN PATENT DOCUMENTS 2207387 2/1972 Fed. Rep. of Germany ... 128/303.1

OTHER PUBLICATIONS

"Heat Sink Protection for Endotracheal Tube Cuffs–$CO_2$ Laser", Le June, Jr. et al., Presented to American Broncho Esophagological Association, May 4, 1982, Palm Beach, Fla.

Primary Examiner—Henry J. Recla
Assistant Examiner—Karin M. Reichle
Attorney, Agent, or Firm—Quarles & Brady

[57] ABSTRACT

An elastomeric back-up pad having a smooth laser-resistant coating thereon is provided for insertion between tissue layers incised during surgical procedures in which a laser is used to incise the tissue. The laser-resistant coating on the pad comprises a mixture of powdered metal which tends to reflect the laser beam and an elastomer which bonds the coating to the pad and imparts a smooth exterior surface to the coating thereby reducing the risk of tissue trauma as the pad is inserted between the tissue layers.

3 Claims, 3 Drawing Figures

LASER-RESISTANT BACK-UP PAD

FIELD OF THE INVENTION

This invention relates generally to laser-resistant materials and more particularly to a laser-resistant back-up pad for use during laser surgery to protect the tissue from inadvertent laser impaction.

BACKGROUND OF THE INVENTION

Lasers are now commonly employed by surgeons to incise tissue during various surgical procedures in place of conventional scalpels. In particular, lasers are often employed where the surgical procedure requires a shallow incision so as to prevent damage to underlying tissue. When a laser is employed to make a shallow tissue incision, past practice has been to interpose damp surgical gauze between each tissue layer once each tissue layer has been exposed so as to protect the tissue from inadvertent laser impaction. However, the use of damp surgical gauze between tissue layers has not proven satisfactory to provide adequate protection to the tissue against inadvertent laser impaction. While the wet gauze is effective to absorb any stray components of the laser beam, once the gauze dries, it will likely combust upon laser impaction or allow the beam to pass unimpeded. To avoid the risk of gauze ignition and/or inadvertent laser impaction, either the surgeon or assisting personnel must periodically dampen the gauze, thus requiring interruption of other more important activities.

It is an object of the present invention to provide a laser-resistant back-up pad for insertion between the layers of tissue incised during laser surgery to protect the tissue from inadvertent laser impaction;

It is yet another object of the present invention to provide a laser-resistant back-up pad having a smooth, laser reflective coating permanently applied to the surface of the pad thereby enabling easy pad insertion between the layers of laser-incised tissue with reduced risk of tissue trauma.

BRIEF SUMMARY OF THE INVENTION

Briefly, in accordance with the preferred embodiment of the invention, a laser-resistant back-up pad for insertion between the layers of tissue incised during laser surgery for protecting the tissue against inadvertent laser impaction comprises an elastomeric substrate typically configured of a sheet of silicone rubber or the like. To render the silicone rubber sheet permanently laser-resistant, the sheet surface is covered with a coating comprised of a mixture of an elastomer solution such as a silicone rubber solution and a reflective material which may be a powdered metal such as aluminum. The reflective material within the coating mixture tends to reflect the laser beam while the elastomer solution causes the coating to be smooth and to be permanently bonded to the silicone rubber sheet. In certain instances, it may be desirable to apply a layer of dampened gauze above the laser-resistant coating on the pad for purposes of fluid absorption and to provide additional tissue protection against laser impaction.

BRIEF SUMMARY OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawings in which:

DETAILED DESCRIPTION OF THE PREFERRED EMBODIMENT

Figure 1:
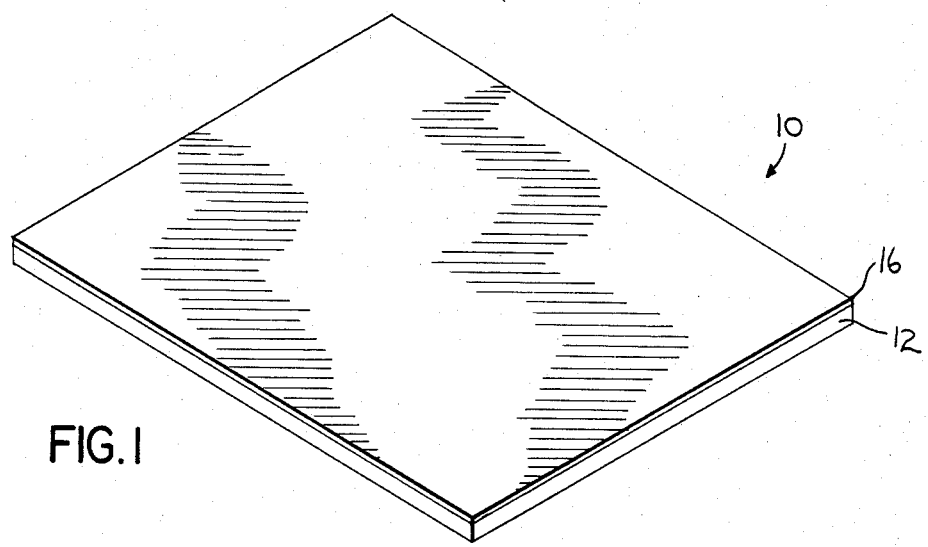
FIG. 1 is a perspective view of a laser-resistant back-up pad constructed in accordance with the present invention.
Figure 2:
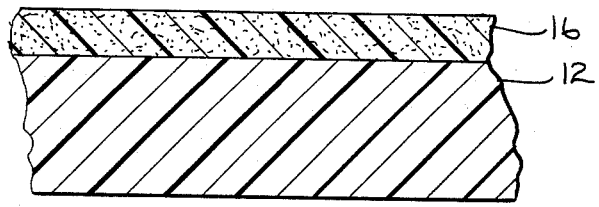
FIG. 2 is a cross section of the pad of FIG. 1 taken along lines 2—2 thereof.

Referring to the figures, FIGS. 1 and 2 are a perspective view and a cut-away view, respectively of a laser-resistant back-up pad 10 for insertion between the layers of laser-incised tissue for protecting the tissue against inadvertent impaction by a laser during laser surgery. Pad 10 is typically comprised of a sheet 12 of elastomeric material such as silicone rubber, latex rubber or polyvinyl chloride. Silicone rubber is preferred because of its relatively high flash point and its relatively inert combustion products in comparison to latex rubber and polyvinyl chloride. In practice, sheet 10 typically has a rectangular shape, although the physical shape of the sheet can take on any other geometric form. The particular shape of the pad is selected in accordance with the shape of the incision into the tissue whose layers are to be protected by the pad. For example, if the surgical procedure required an arcuate incision, the pad might be "D" shaped rather than rectangularly shaped as shown in FIG. 1.

To render pad 10 laser-resistant so that the pad can tolerate inadvertent impaction of the laser beam and deflect the laser beam away from the underlying tissue, sheet 12 has its exterior surface permanently covered with a smooth, laser-reflective coating 16. Laser reflective coating 16 is comprised of a mixture of an elastomer solution, such as a silicone rubber solution, and a reflective material which is preferably a powdered metal, such as aluminum, with the ratio of powdered metal to elastomer solution being between 1 to 1 and 3 to 1. The powdered metal within the laser-reflective coating 16 tends to reflect the laser beam while the elastomer solution component of the coating mixture causes the coating to permanently adhere to the sheet and to have a smooth exterior surface. A smooth exterior surface on the pad is extremely important as it reduces the risk of tissue trauma upon insertion of the pad between the tissue layers.

Laser-resistant coating 16 may be applied to sheet 12 by dipping the sheet in a bath of the coating mixture or painting the sheet with the coating solution and then baking the sheet with the coating solution thereon in an oven of sufficient temperature to cure the coating compound. The two steps of dipping or painting and then baking are repeated until the thickness of the laser resistant coating 16 (which is exaggerated in FIG. 2 for purposes of illustration) is of sufficient thickness to prevent a laser beam from passing through the coating and impacting the elastomeric pad. The step of baking sheet 12 with coating 16 thereon to cure the coating can be eliminated when the elastomer solution component of the laser-resistant coating is a room temperature vulcanizing (RTV) silicone rubber solution.

Figure 3:
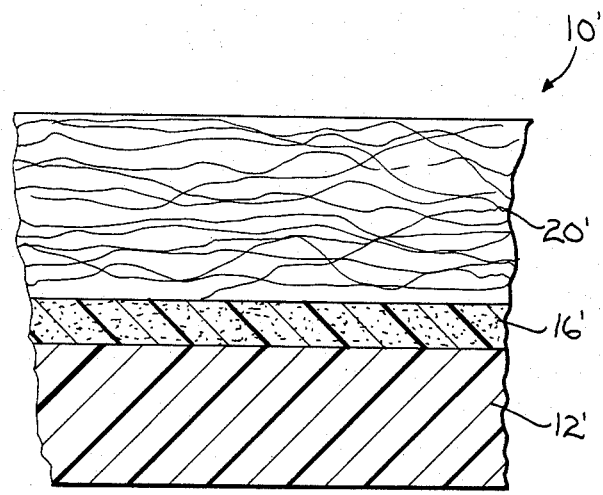
FIG. 3 is a cross sectional view of an alternate preferred embodiment of a laser-resistant pad.

A cross sectional view of an alternate preferred embodiment 10' of a laser-resistant back-up pad for insertion between layers of laser-incised tissue is illustrated in FIG. 3. Laser-resistant back-up pad 10', like laser-resistant back-up pad 10 illustrated in FIGS. 1 and 2, is comprised of a silicone rubber substrate or pad 12' having a smooth laser reflective coating 16' permanently bonded to the exterior surface of the substrate. Laser reflective coating 16' of FIG. 3 is identical to laser reflective coating 16 of FIG. 1 and is applied to pad 12' in the same manner that coating 16 is applied to pad 12. Covering the outwardly exposed surface of coating 16' is a layer of surgical gauze 20' which is typically dampened during actual use of the back-up pad 10'. The dampened gauze 20' acts not only to absorb tissue secretions but also provides a further barrier against laser impaction of the tissue underlying the back-up pad. When back-up pad 10' is employed during laser surgery, care must be taken to keep gauze 20' damp, otherwise a dry layer of gauze may ignite if impacted by the laser beam. In some instances, it may be desirable to have a layer of relatively thick elastomer above the laser reflective coating 16' instead of the gauze; thus making the pad 10' reversible.

The foregoing describes an improved laser-resistant back-up pad for insertion between layers of laser-incised tissue to protect the tissue against inadvertent impaction by a laser beam.

While only certain preferred features of the invention have been shown by way of illustration, many modifications and changes will occur to those skilled in the art. It is, therefore, to be understood that the appended claims are intended to cover all such modifications and changes as fall within the true spirit of the invention.

What is claimed is:

1. A laser-resistant back-up pad for insertion between the layers of tissue incised by a laser during surgery comprising:
    an elastomer substrate having a first surface adapted to face the interior of the body of the patient and an opposite second surface adapted to face the exterior of the body of the patient;
    a smooth laser-reflective coating comprised of a mixture of an elastomer and a laser-reflective material permanently bonded to the second surface of said elastomer substrate; and
    a layer of liquid absorbing non-laser reflective material bonded to said coating such that said laser reflective coating is sandwiched between said elastomer substrate and said liquid absorbing layer.

2. A laser-resistant back-up pad of claim 1 in which the elastomer substrate is of silicone rubber.

3. A laser-resistant back-up pad of claim 1 in which the layer of liquid absorbing non-laser reflective material is gauze.

* * * * *